June 16, 1936. R. H. KISTLER Plant Pat. 183
ROSE
Filed Aug. 21, 1935
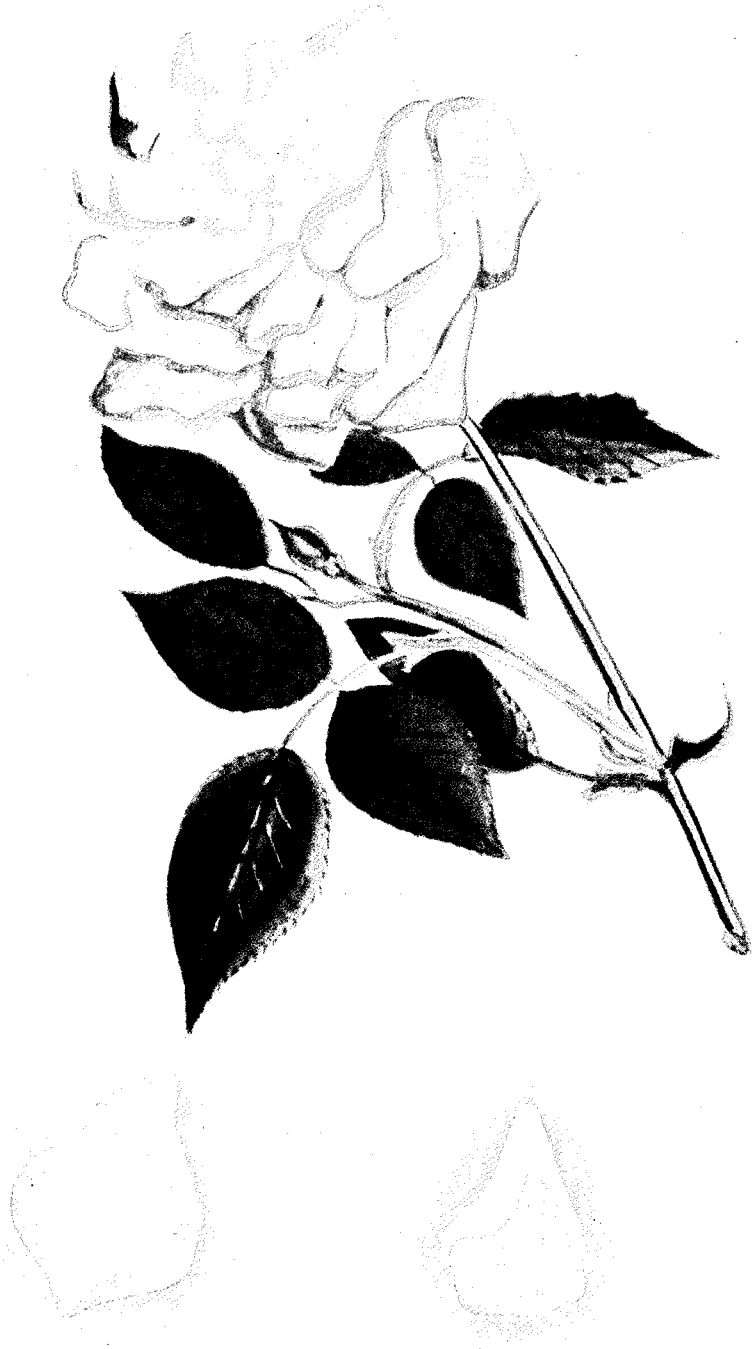
INVENTOR.
R. H. Kistler
By L. F. Randolph Jr. Atty.

Patented June 16, 1936

UNITED STATES PATENT OFFICE

183

ROSE

Robert H. Kistler, Houston, Tex.

Application August 21, 1935, Serial No. 37,231

1 Claim. (Cl. 47—61)

The present discovery relates to a new and distinct rose plant, a large flowering hybrid tea rose, originating as a sport of the Red Radiance.

The predominating feature of novelty of this rose resides in its coloring consisting in the petals that are a deep rose red being splashed and speckled or dotted with white, the outer petals being larger than the inner petals and showing more of the white. Some of the white dots are substantially round while others are more or less elongated, and with the larger splashes of the white the petals are well marked with the white coloring from their bases to their outer edges, and give a general appearance of a red and white rose. This characteristic is permanent during the whole life of the flower and gives it a novel appearance not heretofore found in garden roses.

The deep rose color is between "Sweet Brier" and "Rose Neyron", on plate 1, line 4 of Maerz & Paul's Dictionary of Color; the white is a snow or chalk white, about like 41A1 or 25A1 of Maerz & Paul, supra; and the yellow is between "Marguerite" and "Reed" or 10G1, Maerz & Paul, supra. The other colors mentioned hereafter refer to their ordinary dictionary definitions.

The plant has been asexually propagated and the novel characteristics have been found to be fixed in reproduction. Also, this rose has been extensively tested as a garden rose and for potculture for florists' use and it has been found admirably suited to both uses. The plant is a vigorous grower, strong, upright, and will bloom continuously from early spring until late fall.

For the purposes of specific disclosure, the following description of this new plant is given by way of summary:—

Parentage:—

Sport.

*Parent variety.*—Red Radiance.

Classification:—

Botanic (name strains) and under which it will be in commerce, *hybrid tea rose.*

*Flower*

Blooming habit:—

Location where observations were made, date and time of day.—At 1401 Nashua St., Houston, Texas, and later at 2902 Yale St., Houston, Texas. Observations made in March 1934 and 1935, at six o'clock in the morning.

*Recurrent.*—Continuous, blooms from early spring until frost.

Bud:—

*Size.*—Large.

*Form.*—Globular. It is unaffected by wet or hot weather.

*Color.*—When sepals first divide, when they begin to unfurl, and when half blown, deep rose red dotted and splashed white, both inside and reverse of petals. The red is, as heretofore stated, between "Sweet Brier" and "Rose Neyron", on plate 1, line 4 of Maerz & Paul's Dictionary of Color, and the white a snow or chalk white, about like 41A1 or 25A1 of said Dictionary of Color.

*Sepals.*—Serrated, branched, curl back as bud opens.

*Calyx.*—Shape—funnel. Size—broad. Aspect—smooth. Odor when rubbed—pleasant fruity odor.

*Peduncle.*—Length — long. Aspect — smooth. Color—medium green. Strength—stiff, erect. No thorns, prickles or needles.

*Opening.*—The bud opens well. Is not affected by adverse conditions.

Bloom:—

*Size.*—Large. Average size when fully expanded about 3½ inches.

*Borne.*—Singly.

*Stems.*—Long, strong.

*Form.*—When first open—globular. Permanence—petals curl back.

*Petalage.*—Double (full but open center). Number of petals under normal conditions—thirty.

*Color.*—Center of flower and the outer petals rose red dotted and splashed with white. Base of petals (aiglet)—yellow. The red is, as heretofore stated, between "Sweet Brier" and "Rose Neyron" on plate 1, line 4 of Maerz & Paul's Dictionary of Color, the white about like 41A1 or 25A1, and the yellow between "Marguerite" and "Reed" or 10G1 of said Dictionary of Color. Inside and reverse of petals—rose red dotted and splashed with white and this is the tonality from a distance.

*Discoloration.*—General tonality at the end of the first, second and third day the same.

Petals:—

*Texture.*—Thick. Is not affected by wet weather, but in hot weather the red coloring fades slightly.

*Appearance.*—Inside and outside—shiny.

*Form.*—Oval.

*Arrangement.*—Imbricated (regularly arranged shinglelike), quartered. Petaloids in center—few.

*Persistence.*—Drop off cleanly.

*Fragrance.*—Moderate. Nature—"Old Rose perfume".

*Lasting quality.*—On the plant—long. As cut flower—very long.

Genital organs:—

*Stamens, anthers.*—Medium. Color—yellow. Arrangement—regular around styles.

*Stamens, filaments.*—Long. Color—yellow.

*Pollen.*—Lemon yellow.

*Styles.*—Bunched; uneven medium length; thin.

*Stigmas.*—Color—yellow.

*Ovaries.*—All enclosed in calyx.

Fruit:—

Variety is fertile with its own pollen.

*Form.*—Flat headed.

*Aspect.*—Smooth.

*Color at maturity.*—Russet brown.

*Sepals.*—Permanent; recurved, spear-shaped.

*Plant*

Form:—

Bush.

Growth:—

Vigorous, branching.

Foliage:—

Five leaflets, normally, but frequently only three next to the bud.

*Size.*—Large.

*Quantity.*—Normal.

*Color.*—New foliage: Upper side—bronzy. Under side—light bronze. Old foliage: Upper side—normal green. Under side—light green. The veins and serrations a deep red, contrasting sharply with the color of the rest of the leaf.

*Shape.*—Oval pointed.

*Texture.*—Upper side—smooth. Under side—rough. Ribs and veins—ordinary.

*Edge.*—Serrated (saw-toothed).

*Serration.*—Single, small, sharp.

*Rachis.*—Color—green. Under side—prickles.

*Stipules.*—Medium, smooth.

*Disease resistance.*—Susceptible to black spot, the old foliage showing black spot in bad, wet weather.

Wood:—

*New wood.*—Color—light green. Bark—smooth.

*Old wood.*—Color—green. Bark—smooth.

Thorns:—(N. B.—Thorns are divided into thorns, prickles and short needles.)

*Thorns.*—Quantity: On main stalks from base—few. On laterals from stalk—few. Form—narrow base, medium length, hooked downward. Color when young: Green and red. Position—irregular.

*Prickles.*—Quantity: On main stalk—none. On laterals—none.

*Short needles.*—Quantity: On main stalk—none. On laterals—none.

The main identification marks or traits are the brilliant deep rose color of the petals splashed and dotted with white, some of the dotted portions being round, others oval, others elongated and in some instances a petal will have a clear white streak from top to base, the larger outer petals having larger white splashings than the smaller inner petals. From a distance, of say fifteen feet, the general appearance is of a large red rose splashed and dotted with white.

The keeping quality of the bloom is good, usually a day and a half for buds to become half blown another day to open, and another day to day and a half before the petals begin to drop.

The bud on the bush in the field stands up beautifully in hot or cold, wet or dry weather.

I claim:—

The new and distinct variety of rose plant of the hybrid tea rose class, as described, characterized by the petals being of a deep rose base color with dots and splashes of white, as shown.

ROBERT H. KISTLER.